United States Patent [19]

Wilhelms et al.

[11] Patent Number: 4,592,997
[45] Date of Patent: Jun. 3, 1986

[54] PROCESS FOR THE DETECTION OF THE PRESENCE OF AN ALLERGY AND FOR THE SPECIFIC DETECTION OF THE ALLERGEN RESPONSIBLE FOR THE ALLERGY

[75] Inventors: Otto-Henning Wilhelms, Weinheim-Rittenweier; Peter Stahl, Bernried; Peter Wunderwald, Haunshofen, all of Fed. Rep. of Germany

[73] Assignee: Boehringer Mannheim GmbH, Mannheim-Waldhof, Fed. Rep. of Germany

[21] Appl. No.: 476,452

[22] Filed: Mar. 17, 1983

[30] Foreign Application Priority Data

Mar. 26, 1982 [DE] Fed. Rep. of Germany ....... 3211254

[51] Int. Cl.$^4$ .................... C12Q 1/38; G01N 53/00
[52] U.S. Cl. ........................ 435/23; 435/29; 435/7
[58] Field of Search ............... 436/513, 519; 435/23, 435/29

[56] References Cited

U.S. PATENT DOCUMENTS

| | | | |
|---|---|---|---|
| 4,016,042 | 4/1977 | Svendsen | 435/23 |
| 4,252,715 | 2/1981 | Aurell et al. | 435/23 |
| 4,276,375 | 6/1981 | Claeson et al. | 435/23 |
| 4,279,810 | 7/1981 | Claeson et al. | 435/23 |

FOREIGN PATENT DOCUMENTS

| | | |
|---|---|---|
| 0014929 | 2/1980 | European Pat. Off. . |
| 128691 | 7/1975 | Fed. Rep. of Germany . |
| 3147763 | 6/1983 | Fed. Rep. of Germany . |
| 2315695 | 1/1977 | France . |

OTHER PUBLICATIONS

Chemical Abstracts Band 60, Nr 2, Jan. 20, 1964–Mounter et al.
J. Clin. Invest., vol. 64, Aug. 1979 (457–459; 466–475).
Clin. Chim. Acta, 32 (1971) 67–73.

*Primary Examiner*—Sam Rosen
*Attorney, Agent, or Firm*—Felfe & Lynch

[57] ABSTRACT

The present invention provides a process for the detection of the presence of an allergy and for the specific detection of the allergen responsible for the allergy, based on the cellular principle, wherein leukocytes of a sample to be investigated are incubated with an allergen or another stimulation factor of degranulation, such as anti-IgE, in an aqueous medium, the leukocytes are then separated off and the remaining solution is incubated with a compound of the general formula:

$$Y-X-C$$

in which Y is an amino acid or a peptide containing 2 or 3 amino acids, the amino acids optionally carrying a conventional protective group on the amino end, X is arginine or lysine and C is a chromogenic residue, in the presence of a buffer effective at pH 6.3 to 8.0 and the liberation of the chromogenic residue is measured.

16 Claims, No Drawings

PROCESS FOR THE DETECTION OF THE PRESENCE OF AN ALLERGY AND FOR THE SPECIFIC DETECTION OF THE ALLERGEN RESPONSIBLE FOR THE ALLERGY

The present invention is concerned with a process for the detection of the presence of an allergy and for the specific detection of the allergen responsible for the allergy, as well as with a new protease, the activity of which is determined in the scope of the process of the invention.

In the case of allergic patients, increased IgE levels are found in the blood. IgE is also found bound to mast cells and basophils. The allergic reaction is induced by the binding of an allergen to the IgE specific therefor bound to mast cells or basophils.

It is often assumed that this binding of the stimulating allergen to IgE via the so-called "bridging"0 of neighbouring IgE in complex reaction brings about the degranulation of basophilic leukocytes. As is known, the degranulation liberates histamine and a kallikrein-like protease, as well as other substances.

For the diagnosis of allergic diseases, besides the in vivo tests which cause discomfort to the patient and involve a certain risk, in vitro tests are of increasing importance. Commercially available in vitro tests comprise either whole IgE (general nonspecific detection of the presence of an allergy) or specific IgE (detection of the specificity of the IgE present, which is responsible for the allergy). The advantages of these in vitro tests are the relatively rapid carrying out and minimum discomfort to the patients; and the disadvantages are that the IgE concentration in the serum is not necessarily a parameter for the reactivity of mast cells and basophils (liberation ability of various mediators) and that the detection of the specific IgE requires carrier-bound allergens which are changed due to their binding to the carrier. Consequently, the literature gives reports about falsely negative results.

Attempts have already been made to overcome these disadvantages by cellular tests in which the stimulation of sensitive cells with allergens takes place in vitro and the allergen-stimulating histamine liberation is measured. This method includes the actual procedure which brings about the allergic reaction. A disadvantage of this process is, however, the fact that the histamine analysis can only be carried out with great expense and is subject to disturbance.

Furthermore, the allergen-specific liberation of a kallikrein-like protease from leukocytes has already been described. This protease has a pH optimum at 8.5, a specific inhibitability by aprotinin $I_{50}$ of about 50 μg./ml. and 11% inhibition by 0.1 mole/l. STI (soya bean trypsin inhibitor). The determination of this enzyme takes place radiochemically with $^3$H-TAME (tosyl-arginyl methyl ester) since only very little activity is liberated. The liberation of this protease is also said to be able to take place non-specifically with anti-IgE or specifically with allergen.

It is an object of the present invention to provide a process which combines the specificity of the cellular reaction with a relatively simple carrying out and a high sensitivity.

Thus, according to the present invention, there is provided a process for the detection of the presence of an allergy and for the specific detection of the allergen responsible for the allergy, based on the cellular principle, wherein leukocytes of the sample to be investigated are incubated with an allergen or another stimulation factor of degranulation, such as anti-IgE, in an aqueous medium, the leukocytes are then separated off and the remaining solution is incubated with a compound of the general formula:

$$Y-X-C$$

in which Y is an amino acid or a peptide containing 2 or 3 amino acids, the amino acids optionally carrying a conventional protective group on the amino end, X is arginine or lysine and C is a chromogenic residue, in the presence of a buffer effective at pH 6.3 to 8.0 and the liberation of the chromogenic residue is measured.

The present invention is based upon the surprising discovery of a new protease which is liberated from leukocytes non-specifically with anti-IgE or specifically with an allergen when the leukocytes originate from atopic subjects, i.e. allergically-sensitised persons. The new protease, which is clearly different in its properties from the known kallikrein-like protease from leukocytes, splits chromogen residue-carrying peptides with a good activity. Since leukocytes from atopic subjects give a 5 to 15 times higher production of this protease in comparison with leukocytes from healthy persons, by determination of the activity of this protease there can be provided a more sensitive and quicker allergy test of high specificity.

The new protease from leukocytes, which is also a subject of the present invention, has a specific inhibitability by aprotonin $I_{50}$ of 1 mg./ml. and a specific inhibitability by STI of 50 to 100% at 0.05 mMole/liter. The protease is stable for up to about 100 hours after the liberation so that the measurement can also be carried out a considerable time after the blood sampling, since the cells themselves are also relatively stable. It has a broad pH optimum between about 6.8 and 8.2 determined under the conditions indicated in Example 1.

The substrate of the leukocyte protease used according to the present invention with the general formula $Y-X-C$ contains as C one of the known chromogenic residues which is split off by the new leukocyte protease and is then determined quantitatively according to the present invention. C is preferably a p-nitroaniline residue. In the scope of the invention, the chromogenic residue is a residue which, after splitting off, may be converted into a coloured compound, optionally by the reaction with another compound, or which is coloured itself. The residue Y preferably contains the sequence Gly-Pro.

Especially preferred compounds of the general formula $Y-X-C$ include tosyl-glycyl-prolyl-arginine-p-nitroanilide acetate (commercially available under the designation Chromozym TH), as well as the corresponding compound in which the arginine is replaced by lysine. The compounds $Y-X-C$ can also be used in carrier-bound form.

The process according to the present invention has an unusually wide applicability. Thus, for example, with the use thereof, an ampicillin allergy was demonstrated, which is especially surprising because this finding cannot be explained by the previously known release mechanisms of the allergic reaction. In addition, a metal allergy towards nickel or chromium ions could be demonstrated.

In order, according to the present invention, to be able to detect an allergy, it is merely necessary to obtain washed leukocytes from the person to be investigated, to incubate these with a specific allergen or a non-specific other stimulation factor of degranulation, for example anti-IgE, after the incubation to separate off the leukocytes from the supernatant, to add the substrate and the buffer and, after some time, to determine the liberated chromogen. If, for the incubation, a specific allergen is used, then an increased production of the leukocyte protease according to the present invention is only obtained when the leukocytes are sensitised against this allergen.

Non-specific stimulation factors of degranulation, apart from anti-IgE, have already been described in comparatively large numbers, for example by A. L. DeWeck (Perspective in Allergy Intern. Congress of Chemotherapy, Florence, 1981).

The production of the purified leukocytes used for the process according to the present invention is carried out by methods known to the expert, which do not have to be described here in more detail. Not only the dextran method of Prof. Dr. H. Friemel (Immunologische Arbeitsmethoden, pub. Gustav Fischer Verlag, Stuttgart, 1980) but also the ficoll method of N. R. Rose and H. Friedmann (Manual of Clinical Immunology ASM, Washington D.C., 1980) can be used for the granulocyte enrichment. The cell suspension obtained is preferably mixed with an appropriate buffer, centrifuged at about 300 to 800 g and the sediment suspended in fresh buffer. The washing can, if desired, be carried out repeatedly. For the determination batch, the cell suspension should preferably contain $10^6$ to $10^8$ cells per ml. Instead of leukocytes, the process of the present invention can make use of mast cells.

The buffer used according to the present invention can be any buffer effective in the given pH range, tris buffer having proved to be very suitable.

The duration of the first incubation step, in which the leukocytes are reacted with, for example, anti-IgE, or an allergen, depends upon the temperature employed. At 37° C., it is preferable to incubate for about 60 minutes. The separation of the leukocytes after the incubation is carried out by known methods, for example by centrifuging at 30000 q for 10 minutes. The centrifuge supernatant thereby obtained is mixed directly with the substrate of the general formula Y—X—C and again incubated. For the determination of the measurement value, a comparison sample is preferably also used which, instead of the anti-IgE or allergen solution, has a corresponding amount of buffer solution added thereto.

The measurement of the chromogen is carried out by means of the optical methods known to the expert, either in the visible or in the UV range, depending upon the colour of the residue split off.

According to a special embodiment of the process according to the present invention, it is possible, for the first time, also to carry out the determination of a latent allergy risk. In the case of this further developed modification of the process, the cell material to be tested is first incubated with immunoglobulin (IgE). A sensitisation of the cell material is hereby brought, as a result of which, under the conditions of the process according to the present invention, a result is obtained which is the same as in the case of the presence of an allergy. With the same cell material but with the omission of the preincubation with IgE, results are obtained which are the same as in the case of a non-allergic subject. It is, therefore, possible in this manner to differentiate an allergy, latent allergy and acute allergy.

By means of the process according to the present invention, there is provided a simple, rapid and specific determination method which permits the detection not only of an allergy in general but also the detection of a specific allergen, without discomfort thereby being caused to the patients, which must be taken into account in the case of in vivo tests. Therefore, the process of the present invention combines the advantages of the known in vivo test with the advantages of the in vitro test.

The following Examples are given for the purpose of illustrating the present invention:

EXAMPLE 1

Sample of a healthy donor

1.1 Obtaining leukocytes 60 ml. venous blood of a healthy donor were carefully mixed with 30 ml. of a dextran mixture (dextran with average M.W. of 75000 2%; D-glucose 2%, EDTA 20 mmol/liter; gelatine 0.07%) in a polyethylene beaker and transferred to a siliconised separating funnel. After leaving to stand for 60 to 90 minutes at room temperature, the supernatant containing the leukocytes (about 50 ml.) was separated off and mixed with 50 ml. tris buffer mixture of pH 7.6 (tris 22 mmol/liter; sodium chloride 0.12 mol/liter; potassium chloride 5 mmol/liter; gelatine 0.05%; EDTA 1 mmol/liter; D-glucose 0.1%) and centrifuged for 15 minutes at 800 g. After decanting, the cells were washed twice in that, in each case, they were again suspended in 50 ml. of the same buffer mixture (pH 7.6) and, in each case, centrifuged for 15 minutes at 800 g. The cells were then suspended in 10 ml. of the same buffer mixture.

1.2 Protease liberation

Two 0.9 ml. amounts of cell suspension were each transferred to a polyethylene test tube, mixed with 0.4 ml. tris buffer mixture (pH 7.6) and brought to 37° C. in a water-bath. To one sample, there was added 0.1 ml. of anti-IgE solution (Behring-Werke, No. OTNP 04/05, diluted 1:500 with tris buffer mixture; pH 7.6) and to the other sample (the control) there was pipetted 0.1 ml. of tris buffer mixture (pH 7.6) and to both samples there was added 0.1 ml. calcium chloride solution (4 mmol/liter in isotonic sodium chloride solution; pH 7.6). The two samples were kept for 60 minutes at 37° C., then each was mixed with 0.5 ml. ice-cold EDTA solution (0.1 mol/liter in isotonic sodium chloride solution; pH 7.6) and centrifuged for 10 minutes at 4° C., and at 30000 g, the supernatant being pipetted off immediately after stopping the centrifuge.

1.3 Protease testing

To 0.5 ml of the supernatant was added 0.5 ml. of 1.5 mmol/l. Chromozym TH solution (1 bottle BM 199664 dissolved in 5 ml. water). The extinction difference between the two samples was determined after 1, 2 and 3 hours at 405 nm.

1.4 Results

In the 3 hours, in the untreated sample there was found a constant extinction increase of $\Delta E/h$ of 0.020 and in the sample treated with anti IgE a $\Delta E/h$ of 0.065. Thus anti-IgE treatment of the cells led to an extinction increase of $\Delta E_{405\ nm}/h = 0.045$.

Remarks

In blood of non-allergic donors, with anti-IgE no value above $\Delta E/h=0.1$ was observed using the method of this example. In individual cases, a constant extinction increase was observed over 20 hours.

EXAMPLE 2

Sample of a donor with proven allergy to ampicillin

2.1 Detection of the presence of an allergy by anti-IgE stimulation

Protease liberated by anti-IgE in a manner corresponding to that of Example 1.2 from 0.9 ml. of the leukocyte suspension obtained according to Example 1.1 of a donor allergic to ampicillin (measurement value: $\Delta E/h=0.805$) gave, in comparison with a comparative sample not stimulated with anti-IgE (measurement value: $\Delta E/h=0.085$), an additional extinction change of $\Delta E/h=0.720$ during the first three hours after the start of the reaction with Chromozym TH.

Thus, from 1 ml. of blood, about 1.6 mU Chromozym TH-hydrolysing activity were liberated.

2.2 Detection of the presence of an ampicillin allergy by ampicillin stimulation 0.9 ml. of the leukocyte suspension obtained according to Example 1.1 was stimulated according to Example 1.2 but, instead of 0.1 ml. anti-IgE solution, 0.1 ml. ampicillin/serum albumin solution (ampicillin 5 mg./ml., human serum albumin 5 mg./ml.) was used for the liberation of the protease. The protease liberated by ampicillin (measurement value: $\Delta E/h=0.893$) gave, in comparison with the control not treated with ampicillin (measurement value: $\Delta E/h=0.335$), an additional extinction change of $\Delta E/h=0.558$.

Remarks

Serum albumin is not necessary for the liberation of the protease with ampicillin.

EXAMPLE 3

CBO-Gly-Pro-Arg-pNA as substrate

From two 0.9 ml. amounts of leukocyte suspension obtained according to Example 1.1 from the blood of a healthy donor, there was obtained protease according to Example 1.2, after anti-IgE stimulation, as centrifuge supernatant. The testing of the protease took place as in Example 1.3 but in the case of one sample, instead of Chromozym TH, there was added an equimolar amount of CBO-Gly-Pro-Arg-pNA. Within the first 3 hours equal $\Delta E/h$ values ($\Delta E/h=0.067$) were measured.

EXAMPLE 4

Tos-Gly-Pro-Lys-pNA (Chromozyme PL) as substrate

The activity of two samples treated in parallel according to Example 1 was determined with Chromozym TH and with an equimolar amount of Chromozym PL. With Chromozym PL, there was found $\Delta E/h=0.052$ and with Chromozym TH $\Delta E/h=0.048$.

EXAMPLE 5

Phe-Pip-Arg-pNA as substrate

The protease activity of two samples treated in parallel according to Example 1 was determined with Chromozym TH and with an equimolar amount of S 2238. With S 2238 there was determined $\Delta E/h=0.037$ and with Chromozym TH $\Delta E/h=0.048$.

EXAMPLE 6

The method was carried out as described in Example 1.

Test persons

I. Allergic subject: allergic symptoms (running eyes, sneezing etc.) upon entering a horse stable or in the neighbourhood of a sweating horse. Assumed allergen: horse dust.

II. Non-allergic subject: no allergic symptoms known.

Test

Cell concentration allergic subjects: $5 \times 10^7$ cells/ml.
non-allergic subjects: $4 \times 10^7$ cells/ml.
Initiation of the degranulation reaction with
(a) anti-IgE diluted 1:500→0.1 ml./1.5 ml. test
(b) horse epithelium of the firm Allergopharm diluted 1:100

Dilutions: 1:100, 1:1000, 1:10000→0.1 ml./1.5 ml. test.

Results

1. Non-specific initiation of the allergic reaction by anti-IgE, i.e. presence of an allergy:
allergic subjects: $\Delta E\ 405/hr=1.344$
non-allergic subjects: $\Delta E\ 405/hr=0.038$
2. Specific initiation of the allergic reaction by horse epithelium allergen in the case of allergic subject I:
horse epithelium ellergen
diluted 1:100: $\Delta E\ 405/hr=1.122$
diluted 1:1000: $\Delta E\ 405/hr=1.611$
diluted 1:10000: $\Delta E\ 405/hr=1.598$.

EXAMPLE 7

7.1 Obtaining leukocytes 60 ml. of fresh venous whole blood from healthy donors or atopic subjects were placed in a 100 ml. polyethylene Erlenmeyer flask in which had been placed a mixture of 12.5 ml. dextran solution (average mol. weight 75000), 12.5 ml. D-glucose solution (6%) and 6.0 ml. EDTA solution (100 mM), as well as 2.5 ml. gelatine solution (2%).

After mixing up, portions each of about 20 ml. were transferred into polypropylene-serum-plasma filters (monovettes, firm Sarstedt, Order No. 53,422; 25 ml.) and subsequently left to stand for about 60 to 90 minutes at ambient temperature.

Thereafter, the plasma supernatant (in all about 45 to 50 ml.) was separated from the erythrocyte sediment. 100 μl. of the supernatant were removed for a cell count (leukocytes and erythrocytes using a Coulter counter). Subsequently, the supernatant was diluted about 1:2 with ice-cold tris buffer (6 mM) (pH 7.6)+EDTA (1 mM)+gelatine (0.05%), centrifuged for 15 minutes at $800 \times g$, again washed with the same buffer and then resuspended with tris buffer (6 mM)+glucose (0.1%) to give about 40 ml. Subsequently, 100 μl. of the cell suspension were again taken for a renewed counting.

7.2 Carrying out of the reaction 0.9 ml. amounts of the leukocyte cell suspension were transferred into polyethylene test tubes, mixed with 0.4 ml. tris buffer mixture with an addition of glucose (pH 7.6) and brought to 37° C. in a water-bath and each mixed with 0.1 ml. of an anti-IgE solution (Behringwerke, No. OTNP 04/05, diluted 1:500 with tris buffer mixture: pH 7.6) or correspondingly with, in each case, 0.1 ml. of allergen solution (end concentration in the whole batch calculated to 100, 10 and 1 µg./ml.) and subsequently mixed with, in each case, 0.1 ml. calcium chloride solution (4 mM in isotonic sodium chloride solution; pH 7.6).

Control samples without anti-IgE or allergen stimulus each had added thereto a corresponding 0.1 ml. amount of tris buffer mixture (pH 7.6).

The samples were incubated for 60 minutes at 37° C., then each was mixed with 0.5 ml. ice-cold EDTA solution (10 mM/l. in isotonic sodium chloride solution; pH 7.6) and centrifuged for 10 minutes at 4° C. and at 1500×g. After stopping the centrifuge, the supernatant was pipetted off.

7.3 Analysis

Proteinase

For the measurement of the proteolytic activity, 0.5 ml. amounts of the cell supernatant, which had been stored for a maximum of 15 min./4° C. after separation of the cells, were mixed with 0.7 ml. tris buffer (0.075M; pH 7.6) and 0.3 ml. Chromozym TH solution ($1.5 \times 10^{-3}$M; Boehringer Mannheim, Order No. 199664, in each case 1 bottle dissolved in 5 ml. water). For the determination of the non-specific substrate splitting by (a) proteinases in the allergen extracts or
(b) in the anti-IgE antiserum or
(c) by the working buffer corresponding aliquots were used parallel to the various cell samples with allergen or anti-IgE addition.

Immediately thereafter, the initial extinctions of the samples were measured at 405 nm and at ambient temperature. Subsequently, the samples were left to stand overnight at ambient temperature (20° to 24° C.) and after about 20 hours the extinction was again read off at 405 nm.

A measure of the proteinase which can be liberated specifically by allergen or anti-IgE is the corrected extinction. This is the sample measurement value minus the extinctions for (a) a non-specific substrate splitting by allergen or anti-IgE solution, as well as
(b) the extinction in the "control samples without allergen or anti-IgE stimulus" minus the extinction for the sample of Chromozym TH+buffer.

7.4 Atopic subjects

Leukocytes from a donor with obvious symptoms of hay fever were obtained, reacted and analyzed as is described in 7.1 to 7.3. After an incubation of 20 hours at ambient temperature, the extinction was clearly increased from 0.030 (spontaneous, buffer-induced liberation) to 0.185 (allergen I-induced liberation). From the result obtained, it clearly follows that admittedly allergen I (ray grass) but not allergen II (Alternaria) brought about an unmistakable liberation of proteinase from the leukocytes.

In the same way, after stimulation with anti-human IgE, a clear liberation ($\Delta E_{405}$: 0.197) was ascertained.

EXAMPLE 8

Detection of latent allergy

The test system according to Example 1 was used. The investigated test cell suspensions ($3 \times 10^7$ cells/ml.) were obtained from a latent allergic subject as donor. The process of Example 1 was repeated with this cell suspension. In a second batch, a further amount of the test cell suspension was preincubated for 30 minutes at 37° C. with a human serum enriched with IgE. Thereafter, the cells were washed twice with tris buffer and then further treated as described in Example 1. The following Tables show the results obtained:

| anti-IgE | | 1 hr. | 2 hr. | 3 hr. | 20 hr. |
|---|---|---|---|---|---|
| − | | 0.270 | 0.320 | 0.375 | 1.900 |
| + | | 0.390 | 0.500 | 0.640 | 3.500 |
| ΔE | | 0.120 | 0.180 | 0.265 | 1.600 |
| +IgE | − | 0.250 | 0.260 | 0.275 | 1.100 |
| +IgE | + | 0.580 | 0.930 | 1.300 | 7.100 |
| | ΔE | 0.330 | 0.670 | 1.025 | 6.000 |

The results show that, in the case of incubation with IgE, an extinction difference is obtained which corresponds to the presence of an allergy, whereas in the case of the absense of IgE, the extinction difference indicates no allergy.

We claim:

1. A process for detection of the presence of an allergy and for determination of a specific allergen responsible for that allergy in a sample which comprises leukocytes, said process comprising determination of a protease liberated from said leukocytes in the presence of allergens, said protease characterized by specific apritonin $I^{50}$ inhibitability of about 1 mg/ml, specific soyabean trypsin inhibitor inhibitability of about 50 to about 100% at 0.05 m Mole/liter of said inhibitor, and a pH optimum of from about 6.8 to about 8.2, determination comprising the steps of incubating leukocytes of the sample to be investigated with an allergen or other stimulation factor of degranulation to liberate said protease, separating and removing the leukocytes from the incubated sample, and incubating the solution after removal of the leukocytes with a compound of general formula:

$$Y-X-C$$

in which Y is an amino acid or a peptide containing 2 or 3 amino acids, X is arginine or lysine and C is a chromogenic residue, in the presence of a buffer effective at pH 6.3 to 8.0, said protease liberating the chromogenic residue, and thereafter measuring the chromogenic residue.

2. The process of claim 1 wherein C represents a p-nitroaniline group.

3. The process of claim 1 wherein the compound used is one in which Y contains the group Gly-Pro.

4. The process of claim 1 wherein the compound is tosyl-glycyl-prolyl-arginine p-nitroanilide acetate or a corresponding compound containing lysine instead of arginine.

5. The process of claim 1 wherein the compound is used in carrier-bound form.

6. The process of claim 1 wherein incubation is carried out in the presence of aprotonin.

7. The process of claim 1 further comprising preincubating the leukocytes of the sample to be investigated, with IgE.

8. The process of claim 2 wherein the compound used is one in which Y contains the group gly-pro.

9. The process of claim 8 wherein the incubation is carried out in the presence of aprotonin.

10. The process of claim 1 wherein X is lysine.

11. The process of claim 1 wherein X is arginine.

12. The process of claim 1 wherein the amino acids carry protective groups.

13. The process of claim 1 wherein anti-IgE in an aqueous medium is used as a stimulation factor of degranulation.

14. A process for detection of the presence of an allergy and a specific antigen which is responsible for that allergy in a sample which comprises leukocytes, said process comprising determination of a protease liberated from said leukocytes in the presence of an allergen said protease characterized by specific aprotonin $I^{50}$ inhibitability of about 1 mg/ml, specific soyabean trypsin inhibitor inhibitability of about 50 to about 100% at 0.5m Mole/liter of said inhibitor, and a pH optimum of from about 6–8 to about 8.2, determination comprising the steps of incubating leukocytes of the sample to be investigated with an allergen or other stimulation factor of degranulation to liberate said protease, separating and removing the leukocytes from the incubated sample, and incubating the sample remaining after removal of the leukocytes with a compound of the general formula:

Y—X—C wherein
Y is an amino acid or a peptide containing 2 or 3 amino acids and includes the group Gly-Pro;
C is a chromogenic residue and represent a p-nitroaniline group; and
X is arginine or lysine whereby the chromogenic residue C is split-off, and thereafter,
testing for the split-off chromogenic residue.

15. The process of claim 14 wherein the amino acids carry protective groups.

16. The process of claim 14 wherein anti-IgE in an aqueous medium is used as a stimulation factor of degranulation.

* * * * *